United States Patent [19]

Umezawa et al.

[11] 4,242,453
[45] Dec. 30, 1980

[54] CULTIVATING STREPTOMYCES TO PRODUCE AN ESTERASE INHIBITOR

[75] Inventors: Hamao Umezawa, Tokyo; Takaaki Aoyagi, Fujisawa; Tomio Takeuchi, Tokyo; Masa Hamada, Hoya; Masaaki Ishizuka, Tokyo, all of Japan

[73] Assignee: Zaidan Hojin Biseibutsu Kagaku Kenkyu Kai, Tokyo, Japan

[21] Appl. No.: 39,094

[22] Filed: May 14, 1979

Related U.S. Application Data

[62] Division of Ser. No. 873,350, Jan. 30, 1978, Pat. No. 4,189,438.

[30] Foreign Application Priority Data

Feb. 8, 1977 [JP] Japan .................................. 52/12119

[51] Int. Cl.³ ............................................ C12P 17/02
[52] U.S. Cl. .................................... 435/123; 435/899
[58] Field of Search .................................. 435/68, 123

[56] References Cited

U.S. PATENT DOCUMENTS

| | | | |
|---|---|---|---|
| 3,629,404 | 12/1971 | Florent et al. .......................... | 435/68 |
| 3,840,516 | 10/1974 | Umezawa et al. ..................... | 435/68 |

*Primary Examiner*—Alvin E. Tanenholtz
*Attorney, Agent, or Firm*—Herbert W. Taylor, Jr.

[57] ABSTRACT

A new physiologically active substance named esterastin is now provided, which inhibits the activity of esterase and is useful as an immunosuppressive drug. Esterastin is produced by cultivating a micro-organism Streptomyces MD4-C1 identified as FERM-P 3723 or ATCC. 31336 in a culture medium under aerobic conditions and recovering it from the resulting culture. Esterastin is the compound having the formula

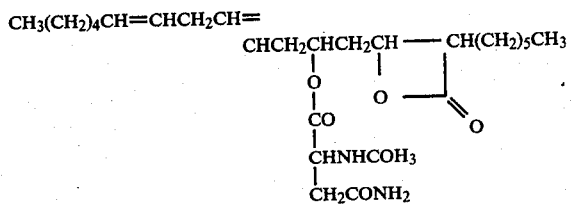

4 Claims, No Drawings

CULTIVATING STREPTOMYCES TO PRODUCE AN ESTERASE INHIBITOR

CROSS REFERENCE TO RELATED APPLICATION

This application is a division of our prior, copending application Ser. No. 873,350 filed Jan. 30, 1978 now U.S. Pat. No. 4,189,438.

SUMMARY OF THE INVENTION

This invention relates to a new physiologically active substance, esterastin, which inhibits the enzymatic activity of esterase. This invention also relates to a process for the production of esterastin and more particularly to a process for the production of esterastin by cultivating a species of the genus Streptomyces in a culture medium to produce and accumulate esterastin and then recovering esterastin from the culture. This invention further relates to an immunosuppressive drug comprising esterastin as the active ingredient.

BACKGROUND OF THE INVENTION

We, the present inventors, recently discovered that a substance active against esterase is present in the culture as obtained by cultivating a microorganism which was isolated from a soil sample collected in the ground of Biseibutsu Kagaku Kenkyu-sho in Shinagawa-ku, Tokyo, Japan and which was designated Streptomyces MD4-Cl. We succeeded in isolating this substance from said culture. As a result of investigation, this substance is found to be a new substance and now named esterastin. We have made extensive research on whether esterastin is useful as a medicine for any purpose. In consequence, we have now found that esterastin is active to reduce the number of the cells forming humoral antibody and also to suppress the cellular immunity. As esterastin is a substance of a very low toxicity, this substance is a physiologically active compound which may be used with safety as a drug to treat diseases caused by the immune reactions such as, for example, contact allergic dermatitis, systemic lupus erythematosus, autoimmune hemolytic anemia, periarteritis nodosa, myasthenia gravis, arthritis, rheumatism and multiple sclerosis and which may be used as an immunosuppressive drug in the surgical operations of transplantation of an internal organ such as heart, kidney and muscle. Esterastin is also expected to be useful as an anti-inflammatory agent because it inhibits the activation of the complement system owing to its esterase-inhibiting activity.

We made systematic research to seek for a physiologically active substance which is inhibitory to the decomposition of p-nitrophenyl acetate by esterase, and during this research we discovered esterastin in the fermentation broth of the above-mentioned microorganism as stated hereinbefore.

Further investigation of esterastin reveals that this substance has the chemical structure shown below.

DETAILED DESCRIPTION OF THE INVENTION

According to this invention, therefore, there is provided a new compound, esterastin, of the following formula:

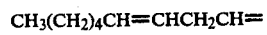

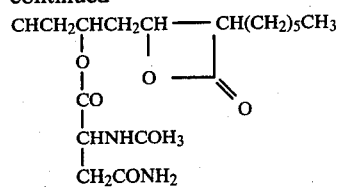

Esterastin is a colorless and powdery substance which is neutral in nature and inhibits the action of esterase and exhibits the following characterizing physico-chemical properties:

(a) having a melting point of 90°–95° C. and a specific optical rotation $[\alpha]_D^{20} + 11°$ (c 1, chloroform), (b) being soluble in pyridine, dimethylsulfoxide, methanol, ethanol, acetone, ethyl acetate, butyl acetate, chloroform and benzene but sparingly soluble in water, petroleum ether and hexane, (c) giving a molecular weight of 506 as measured by mass spectrometry, (d) giving an elemental analysis: C 67.04%, H 9.21%, N 5.56% and O 17.90%, (e) showing an absorption peak $\gamma_{max}$ at 230 nm ($E_1^{cm^1 \%}$ 22.5) in ultra-violet absorption spectrum (in 95% methanol) and (f) showing characteristic absorption bands at 3470, 3350, 2950, 1840, 1730, 1645, 1610, 1545, 1415, 1375, 1325, 1260, 1225, 1185, 1115, 1040, 1020, 975, 920, 900, 880, 840, 810 and 690 cm$^{-1}$ in infra-red absorption spectrum pelleted in potassium bromide.

According to this invention there is also provided a process for the production of esterastin, which comprises cultivating an esterastin-producing strain of the genus Streptomyces under aerobic conditions in a suitable culture medium therefor containing assimilable carbon and nitrogen sources for a period of time sufficient to produce and accumulate esterastin in the culture medium and recovering esterastin from the culture.

The esterastin-producing strain of Streptomyces may be, for example, Streptomyces MD4-Cl as mentioned hereinbefore. This MD4-Cl strain was deposited on Sept. 25, 1976 in a Japanese authorized depository "Fermentation Research Institute, Agency of Industrial Science and Technology", Inage, Chiba-City, Japan, under deposit number FERM-P 3723. This MD4-Cl strain was also deposited on Sept. 20, 1977 in the American Type Culture Collection, Rockville, Md., U.S.A. under ATCC Number 31336.

Cultural and taxonomic characteristics of the MD4-Cl strain are described below.

1. MICROSCOPIC MORPHOLOGY

MD4-Cl strain has branched substrate mycelia from which aerial hyphae develops in the form of open spirals. No whorl-branching is observed. Matured spore chains usually bear more than 10 conical spores. Spores usually measure about 0.6–0.8 by 0.8–1.2 microns in size and have a smooth surface.

2. CHARACTERISTICS OF THE GROWTH ON VARIOUS CULTURE MEDIA

The designation of colors in brackets [ ] mentioned below follows the color standard given in the "Color Harmony Manual" published by Container Corporation of America.

(1) On sucrose-nitrate agar (incubated at 27° C.): Colorless growth bears aerial hyphae of grayish red color [6 ge, Rose Gray] to reddish grey color [5 ge, Rosewood]. No soluble pigment is observed.

(2) On glucose-asparagine agar (incubated at 27°C.): Colorless growth bears aerial hyphae of light reddish brown color [5 ec, Dusty Peach] to bright brownish grey color [3 fe, Silver Gray]. No soluble pigment is observed.

(3) On glycerin-asparagine agar (ISP No. 5 medium, incubated at 27° C.): Colorless to light yellow growth bears aerial hyphae of white to pinkish white color after about 14 days of incubation. No soluble pigment is observed.

(4) On starch-inorganic salts agar (ISP. No. 4 medium, incubated at 27° C.): Colorless growth bears aerial hyphae of bright brownish grey color (3 fe, Silver Gray) to pinkish grey color. No soluble pigment is observed.

(5) On tyrosine agar (ISP No. 7 medium, incubated at 27° C.): Light yellow growth bears aerial hyphae of pinkish white color to reddish grey color [5 ge, Rosewood]. No soluble pigment is observed.

(6) On nutrient agar (incubated at 27° C.): Light yellow growth. Neither aerial hyphae is formed nor soluble pigment is observed.

(7) On yeast extract-malt extract agar (ISP No. 2 medium, incubated at 27° C.): Light yellowish brown to yellowish brown growth bears aerial hyphae of bright brownish grey color to pinkish grey color (7 ig, Rose Taupe). No soluble pigment is observed.

(8) On oat-meal agar (ISP No. 3 medium, incubated at 27° C.): Colorless to light yellow or dull yellow growth bears aerial hyphae of greyish red color [6 ge, Rose Gray] to reddish grey color [5 ge, Rosewood to 5 ig, Rose Taupe]. No soluble pigment is observed.

(9) On glycerine-nitrate agar (incubated at 27° C.): Light yellow to light yellowish brown [3 ie, Camel to 4 ie, Cork Tan] growth bears aerial hyphae of white to brownish white color.

(10) On starch agar (incubated at 27° C.): Colorless growth bears aerial hyphae of brownish white color to light brownish grey color [5 dc. Pussywillow Gray]. No soluble pigment is observed.

(11) On calcium-malate agar (incubated at 27° C.): Colorless growth bears aerial hyphae of white color to faint reddish brown color [5 ec. Dusty Peach] to reddish grey color [5 ge, Rosewood]. No soluble pigment is observed.

(12) On cellulose (incubated at 27° C.): The growth is colorless. Neither aerial hyphae is formed nor soluble pigment is observed.

(13) On gelatin stab: On plain gelatin medium (incubated at 20° C.), the growth is colorless with developing aerial hyphae of white color and with producing soluble pigment of brown color. On glucose-peptone-gelatin medium (incubated at 27° C.), light yellow to light yellowish brown growth with slightly developing aerial hyphae of white color and with producing soluble pigment of dark brown color.

(14) On skimmed milk (incubated at 37° C.): Colorless to light yellow growth bears slightly aerial hyphae of white color. Soluble pigment is very faintly tinged with brown on and since 19th day of the incubation.

3. PHYSIOLOGICAL PROPERTIES (1) Temperature for growth

Growth on starch-yeast agar (comprising 1.0% soluble starch, 0.2% yeast extract and 3.0% agar, pH 7.0–7.2) was examined at 20° C., 24° C., 27° C., 30° C., 37° C. and 50° C. The MD4-Cl strain grew at all temperatures tested, except at 50° C. Optimum temperature for good growth was observed to be in the vicinity of 27° C.–37° C.

(2) Liquefaction of gelatin

Plain gelatin (15%) medium did not liquefy when incubated at 20° C. The gelatin (15%) in glucose-peptone-gelatin medium started to liquefy from about the 5th day of incubation when incubated at 27° C., and the degree of liquefaction was then medium to weak.

(3) Hydrolysis of starch

Starch in inorganic salts-starch-agar medium and in starch-agar medium was hydrolyzed starting from about the 5th day of incubation when incubated at 27° C., and the grade of hydrolysis was medium.

(4) Coagulation and peptonization of skimmed milk

The coagulation of skimmed milk did not commence, but the peptonization started from about the 12th day of incubation when incubated at 37° C. The grade of peptonization was then medium.

(5) Formation of melanoid pigments

Formation of melanoid pigments was observed on trypton-yeast extract broth (ISP No. 1 medium) and on peptone-yeast extract-iron agar (ISP No. 6 medium) when incubated at 27° C. No pigmentation was observed on tyrosine agar (ISP No. 7 medium).

(6) Utilization of carbon sources for growth

Utilization of the under-mentioned carbohydrates was tested in Pridham-Gottlieb agar medium (ISP No. 9 medium) when incubated at 27° C.

Glucose was utilized for growth, but L-arabinose, D-xylose, D-fructose, sucrose, inositol, L-rhamnose, raffinose and D-mannitol were not utilized.

(7) Liquefaction of calcium malate

Calcium malate in calcium malate-agar medium was liquefied around the growth starting from about the 10th day of incubation, when incubated at 27° C. The grade of liquefaction was medium to strong.

(8) Reduction of nitrate

Reduction of nitrate was not observed in aqueous peptone solution containing 1.0% potassium nitrate (ISP No. 8 medium), when incubated at 27° C.

Summarizing the above-mentioned properties of the MD4-Cl strain, it is noted that this strain belongs to the genus Streptomyces and that the aerial hyphae form spirals but do not develop whorl. The surface of spore is smooth under microscopic observation. On various media, the growth has a color of colorless to light yellow or light yellowish brown, with developing aerial hyphae of reddish grey color to pinkish grey color to bright brownish grey color but without producing soluble pigment. Formation of melanoid pigments is positive on trypton-yeast extract broth and on peptone-yeast extract-iron agar medium but is negative on tyrosine agar medium. Proteolysis and starch hydrolysis are of medium grade.

On account of the above-mentioned properties the MD4-Cl strain was compared to known analogous species of Streptomyces with reference to descriptions of International Streptomyces Project (ISP). It is found that the MD4-Cl strain most closely resembles to *Streptomyces lavendulae* (see the "Journal of Systematic Bacteriology" Vol. 18, page 138 (1968), hereinafter referred to as Literature No. 1; and Waksman's "The Actinomycetes" Vol. 2, page 234, referred to as Literature No. 2) and *Streptomyces avidinii* (see the "Journal of Systematic Bacteriology" Vol. 22, page 276 (1972), referred to as Literature No. 3; and the "Antimicrob. Ag. Chemother." page 20 (1963) referred to as Literature No. 4 hereinafter). These two known species were actually obtained and directly compared to the MD4-Cl strain. A summary of the results of the comparison is tabulated below.

cerned with, the difference in the color of aerial hyphae is not significant to distinguish *Streptomyces avidinii* from *Streptomyces lavendulae*. Major differences between these two species are only found as to whether or not the formation of melanoid pigment and coagulation of milk is observed. However, these two species are considered to be very much closely related to each other, as the above-mentioned differences are not the deciding factor to distinguish one species from other species of the genus Streptomyces.

The MD4-Cl strain is found to produce a known antibiotic, streptothricin, and the MD4-Cl strain is well coincident with *Streptomyces lavendulae* except that they are different from each other in the formation of melanoid pigment. On the other hand, the MD4-Cl strain is coincident with *Streptomyces avidinii* in all respects except that the former does not bring about the coagulation of milk.

In view of the above, it is judged that the MD4-Cl

TABLE 1

| Properties | MD4-Cl | Streptomyces lavendulae ISP 5069 | Streptomyces avidinii ISP 5526 |
|---|---|---|---|
| Form of aerial hyphae | Spirales* | Rectiflexibles or Spirales (Literature No. 1: Retinaculiaperti) | Spirales* (Literature No. 3: Retinaculiaperti) |
| Spore surface | Smooth | Smooth (incompletely warty in parts) | Smooth |
| Color of aerial hayphae | Reddish grey to pinkish grey, bright brownish grey | Pinkish grey to bright brownish grey | Reddish grey to pinkish grey, bright brownish grey |
| Color of growth | Colorless to light yellow, light yellowish brown | Colorless to light yellowish brown (tinged with light olive to greyish olive in parts) | Colorless to light yellow, light yellowish brown |
| Soluble pigment | − | − | − |
| Formation of melanoid pigment | | | |
| On ISP No. 1 medium | + (weak) | + (weak) | + (weak) |
| On ISP No. 6 medium | + | + | + |
| On ISP No. 7 medium | − | + | − |
| Hydrolysis of starch | + | + | + |
| Coagulation of milk | − | − | + |
| Peptonization of milk | + | + | + |
| Liquefaction of gelatin | | | |
| in plain gelatin medium | − | − | − |
| in glucose-peptone-gelatin medium | + | + | + |
| Reduction of nitrate | − | − | − |
| Utilization of carbon source | | | |
| Glucose | + | + | + |
| L-Arabinose | − | − | − |
| D-Xylose | − | − | − |
| D-Fructose | − | − | ∓ (Literature No.3: +) |
| Sucrose | − | − | − |
| Inositol | − | − | − |
| L-Rhamnose | − | − | − |
| Raffinose | − | − | − |
| D-mannitol | − | − | − |
| Antibiotics produced | Streptothricin | Streptothricin, MSD-235 | MSD-235 |

Notes:
"∓" means probable non-utilization.
*no formation of spirales is observed in ISP No. 5 medium.

As will be seen from the above Table, the MD4-Cl stain is very similar to *Streptomyces lavendulae* ISP 5069 and *Streptomyces avidinii* ISP 5526. Amongst the strains producing the antibiotic MSD-235, *Streptomyces avidinii* is distinct from *Streptomyces lavendulae* in that the former produces aerial hyphae having a tinge of grey. As far as the results of the above comparisons and the descriptions of Literatures No. 1 and No. 3 are concerned with, the strain belongs to a group of *Streptomyces lavendulae*, and the MD4-Cl strain is now designated as *Streptomyces lavendulae* MD4-Cl.

Mutation of actinoymcetes occurs frequently under either artificial or spontaneous conditions. Accordingly, *Streptomyces lavendulae* MD4-Cl used according to this invention includes all mutants thereof. Furthermore, this invention covers the use of all strains of the genus Streptomyces which produce esterastin.

Esterastin can be produced by aerobic cultivation of spores or mycelia of an esterastin-producing strain of the genus Streptomyces such as Streptomyces MD4-Cl strain (identified as FERM-P 3723 or ATCC. No. 31336.) In carrying out the process of this invention, an amount of spores or mycelia of an esterastin-producing strain is inoculated to a suitable culture medium therefor comprising assimilable carbon and nitrogen sources and is then incubated under aerobic conditions, preferably under submerged aerobic conditions, so that esterastin is produced and accumulated in the culture broth. Generally, nutrient constituents of the culture media commonly employed for cultivation of ordinary actinomycetes can be used for the purpose of this invention. For instance, commercially available glycerin, glucose, lactose, sucrose, starch, maltose, molasses and other carbohydrates as well as fat and oil are useful as the carbon source. Commercially available peptone, meat extract, cotton seed meal (e.g. Pharma-Media), peanut meal, soybean meal, yeast extract, N-Z amine, casein, L-asparagine, sodium nitrate, ammonium nitrate, ammonium sulfate and the like may be useful as the nitrogen source. In addition, sodium chloride, phosphates, calcium carbonate, magnesium sulfate and other inorganic salts can be employed for the salt-additive in the culture medium. Other metal salts and various heavy metal salts may also be added in trace quantities, if required, as long as they are utilized by the esterastin-producing strain and are not detrimental to the production of esterastin. Any of the nutrient materials which are known for cultivation of actinomycetes may be employed in the process of this invention, as far as it is assimilable by the esterastin-producing strain for the production of esterastin.

Particularly, glycerin is preferred as the carbon source and cotton seed meal, L-asparagine and the like are preferred as the nitrogen source. A culture medium comprising 1.5% glycerin, 1.5% cotton seed meal, 0.2% L-asparagine and 0.3% sodium chloride is preferred for use.

For the production of esterastin on a large scale, liquid cultivation is preferred. Any temperature at which the esterastin-producing strain is able to grow and produce esterastin can be employed for the cultivation, but a particularly preferred incubation temperature is in a range of 25° to 35° C. The cultivation is continued for a period of time sufficient to produce and accumulate a sufficient amount of esterastin in the culture medium or broth. For instance, the production and accumulation of esterastin reached a maximum at the end of incubation for 2 to 4 days when a culture medium comprising 1.5% glycerin, 1.5% cotton seed meal, 0.2% L-asparagine and 0.3% sodium chloride (pH 7.4) was prepared and sterilized, followed by inoculation with spores and mycelia harvested from a slant culture of the MD4-Cl strain and by shake-cultivation at 27° C. under aerobic conditions.

Assay of esterastin can be made by determining potency of esterastin to inhibit esterase according to a modification of the method of Yasunori Kobayashi described in a Japanese literature "Seikagaku" Vol. 36, page 335 (1964). Thus, a commercially available, crude lipase preparation obtained from pig pancreas is dissolved to a concentration of 0.5% (by weight) in a 0.05 M phosphate buffered solution (pH 7.0) containing 0.2% "Triton X-100" (a trade name of an emulsifier consisting of a polyethyleneglycol alkylphenylether, a product of Rohm & Haas Co., U.S.A.). 0.03 ml of this lipase solution, 2.92 ml of 0.05 M phosphate buffered solution (pH 7.0) and 0.025 ml of a solution containing an esterastin sample to be assayed are mixed together, and the resulting mixture (2.975 ml) is warmed at 20° C. for 3 minutes and then admixed with 0.025 ml of a solution containing 10 mg/ml of p-nitrophenyl acetate in methanol to start the reaction of p-nitrophenyl acetate with lipase. After the reaction was effected at 20° C. for 30 minutes, absorbance (a) at 400 nm of the resulting reaction solution is measured. On the other hand, absorbance (b) at 400 nm of a control reaction solution obtained from the blank test using the 0.05 M phosphate buffered solution containing no esterastin is measured in the same way as above. Degree (%) of inhibition to esterase is calculated according to the following equation:

$$\text{Inhibition (\%)} = \frac{(b - a)}{b} \times 100$$

In accordance with this assay method, the colorless powder of esterastin (the product of Example 7 hereinafter shown) had a potency such that its $ID_{50}$, namely the dose of giving 50% inhibition to esterase, amounted to 0.0002 mcg/ml.

Esterastin may be produced well by a tank-cultivation method as well as by a shake-cultivation method. For instance, 250–300 l of a liquid culture medium comprising 1.5% Pharma-media, 15% glycerin, 0.3% sodium chloride and 0.2% L-asparagine was placed in a fermentation tank of 570 l-capacity and then sterilized, and thereafter the medium was inoculated with a slant culture of the MD4-Cl strain to an inoculum size of 10% while sterile air was passed at a rate of 250–300 l/minute into the medium which was agitated by a stirrer rotating at 200 r.p.m. The incubation temperature was 27° C. In this experiment, the production of esterastin reached a maximum at the end of 48–72 hours incubation.

Esterastin so produced is present in the fermentation broth and in the mycelia of the MD4-Cl strain. For the recovery of esterastin from the culture of the MD4-Cl strain, the fermentation broth is filtered and the filter cake comprising the mycelia containing esterastin is estracted with a water-miscible organic solvent such as methanol, ethanol and acetone. To recover esterastin from the mycelia, the mycelia cake is extracted twice with a 5–10 fold volume of methanol so that esterastin is transferred from the mycelia into the methanol phase. The resulting methanolic extract is concentrated to dryness under reduced pressure, and the residue is extracted with an organic solvent which is highly capable of dissolving esterastin, for example, chloroform, acetone, bezene, butyl acetate and ethyl acetate. When a large volume of the mycelia cake is treated, it is convenient to extract the mycelia cake with methanol, to concentrate the methanolic extract to dryness under reduced pressure, to extract the resulting residue with chloroform or other organic solvent, to concentrate the resultant extract to dryness under reduced pressure and to treat the resulting crude powder of esterastin with butyl acetate and water according to a known solvent distribution method so that esterastin is extracted into the butyl acetate phase in high purity.

To recover esterastin from the fermentation broth, the fermentation broth containing the mycelia as such is concentrated to dryness under reduced pressure, and the solid residue is then extracted with an organic solvent which is highly capable of dissolving esterastin, for example, methanol, ethanol, dimethylsulfoxide, acetone, butyl acetate and chloroform, so that esterastin is extracted into this organic solvent. When esterastin is to be recovered from a large volume of the fermentation broth filtrate, it is convenient to extract the broth filtrate with a water-immiscible organic solvent which is highly capable of dissolving esterastin, for example, butyl acetate and thereby to dissolve esterastin into the organic solvent (eg. butyl acetate) phase. When the fermentation broth is extracted twice with about a half volume of butyl acetate, substantially the entire amount of esterastin present in the fermentation broth filtrate is transferred and dissolved into the butyl acetate phase. Extraction and purification of esterastin can also be made according to a known counter-current distribution method using two solvents which dissolve esterastin but are immiscible with each other. When the extract of esterastin in butyl acetate so obtained is concentrated to dryness under reduced pressure, there is obtained a crude powder comprising esterastin.

It is also possible to recover esterastin in a favorable yield from a solution containing esterastin dissolved therein, by treating said solution with an adsorbent to make adsorption of esterastin and then treating the adsorbent properly to desorb esterastin therefrom. As suitable adsorbent for this purpose may be used an organic adsorbent such as Amberlite XAD (a non-ionic, highly porous resin, a product of Rohm & Haas Co., U.S.A.) and an inorganic adsorbent such as active carbon, alumina, silica and magnesium silicate (Florosil). For instance, esterastin may be adsorbed by silica gel and eluted therefrom using chloroform-methanol (80:1 by volume). When a crude powder of esterastin which was obtained by the extraction of the mycelia of the MD4–Cl strain with methanol, concentration of the methanolic extract to dryness, extraction of the residue with butyl acetate and concentration of the butyl acetate extract to dryness is subjected to chromatography on silica gel, followed by elution with chloroform-methanol (80:1), esterastin can be obtained in a yield of 90% or more.

For the purification of esterastin, it is effective to subject a crude powder of esterastin to chromatography on silica gel. For instance, substantially pure esterastin is obtained by treating a crude powder of esterastin according to a chromatography on dry silica gel eluted with ethyl acetate as the development solvent. Substantially pure esterastin so obtained may further be purified by re-precipitation from a suitable solvent or mixed solvents such as chloroform-petroleum ether, so that pure esterastin is isolated in the form of a colorless powder. For the purification of esterastin, it is also effective to resort on chromatography on Sephadex LH-20 (a gel-filtration agent, a product of Pharmacia Co., Sweden).

Physico-chemical and biological properties of esterastin of this invention are now described below in more detail.

Esterastin in the form of a colorless powder shows a melting point of 90°–95° C. and a specific optical rotation $[\alpha]_D^{20} + 11°$ (c 1, chloroform). Elemental analysis: C 67.04%, H 9.21%, N 5.56% and O 17.90%. UV absorption spectrum of esterastin in a solution of 0.1 mg/ml of esterastin in methanol exhibits an absorption peak at 230 nm ($E_{1cm}^{1\%}$ 22.5).

IR. absorption spectrum of esterastin pelleted in potassium bromide exhibits characteristic absorption bands at the following wave numbers ($cm^{-1}$): 3470, 3350, 2950, 1840, 1730, 1645, 1610, 1545, 1415, 1375, 1325, 1260, 1225, 1185, 1115, 1040, 1020, 975, 920, 900, 880, 840, 810 and 690.

Mass spectrometry of esterastin shows a molecular ion peak at m/e 506. The molecular ion peak and the values of elemental analysis indicate that esterastin has the empirical formula $C_{28}H_{46}N_2O_6$. This formula has been confirmed by high-resolution mass-spectrometry (Found: m/e 506.3364, Calcd. mol. wt. for $C_{28}H_{46}N_2O_6$: 506.3354).

Esterastin was hydrolyzed in 6 N hydrochloric acid at 100° C. for 18 hours and the hydrolysate obtained was subjected to amino acid analysis in which aspartic acid was detected. Esterastin is readily soluble in pyridine, dimethylsulfoxide, methanol, ethanol, acetone, ethyl acetate, butyl acetate, chloroform and benzene but substantially insoluble in water, petroleum ether and hexane. Esterastin, is positive to Rydon-Smith reaction, Dragendorff reaction and iodine vapor reaction but is negative to Ehrlich reaction, ninhydrin reaction and Sakaguchi reaction.

In a thin layer silica gel chromatography on "Silica Gel G", esterastin gives an Rf value of 0.6 when developed with chloroform-methanol-water (10:1:0.05); and an Rf value of 0.2 when developed with ethyl acetate. Esterastin does not move in a high-voltage paper electrophoresis (3500 volts, 15 minutes) using formic acid-acetic acid-water (25:75:900).

Esterastin of this invention is of a very low toxicity, as shown by the fact that no toxicity was observed at all when a dose of 250 mg/kg (by intraperitoneal injection) was given to mice for estimation of acute toxicity. As described hereinbefore, esterastin at a concentration of 0.0002 mcg/ml exhibits 50% inhibition ($ID_{50}$) to the esterase of pig pancreas. As known substances which inhibit the esterase, there may be mentioned paradoxon and di-isopropyl fluorophosphate etc., which are highly toxic compounds. While, esterastin is not toxic and strongly inhibits the activity of esterase to the extent that esterastin at a low level of $4.1 \times 10^{-11}M$ gives 50% inhibition of esterase when estimated using p-nitrophenyl acetate as the substrate. In these respects, it also can be confirmed that esterastin is a novel substance.

From further tests, it has been found that esterastin has an effect on the immune response in living animals.

The effect of esterastin on the immune response was investigated as follows.

(1) Effect on formation of humoral antibody

Groups of dd/Y mice (5 female mice per group, 6–8 weeks old) were immunized with $10^8$ red blood cells of sheep as the anitgen (in the form of a suspension in physiological saline solution) by intravenous injection to develop the immunity. At the same time, 1 mg, 250 mcg, 62.5 mcg or 15.6 mcg of esterastin (in the form of a suspension in 1% DMSO-saline) per mouse were intraperitoneally injected into the separate groups of mice, respectively. On the 4 days after the immunization, the mice treated were sacrificed, spleen was teased and the number of the antibody-forming cells present in each mouse spleen was enumerated according to the method of Jerne (see N. K. Jerne, A. A. Nordin and C. Henry: "The agar plaque technique for recognizing antibody-producing cells. Cell-bound Antibodies." ed. B. Amos and H. Koprowski pp. 109–122, Wister Institute Press. Philadelphia, 1963). The results of the tests so obtained are shown in Table 2 below.

TABLE 2

Effect of esterastin on antibody formation

| Antigen | Dose of esterastin per mouse | Number of antibody-forming cells per spleen (± S.E.**) |
|---|---|---|
| 10⁸ SRBC* | 0 | 170,000 ± 10,400 |
| " | 1 mg | 45,300 ± 3,300 |
| " | 250 mcg | 52,000 ± 2,300 |
| " | 62.5 mcg | 55,000 ± 5,700 |
| " | 15.6 mcg | 173,000 ± 19,600 |

*SRBC denotes sheep red blood cell.
**S.E. means standard error.

From the results of the above table, it is shown that administration of 1 mg to 62.5 mcg of esterastin to mice remarkably reduces the number of the antibody forming cells.

(2) Effect on cell-mediated immunity

Effect of esterastin on the cellular immunity was tested according to a known Delayed Type Hypersensitivity (D.T.H.) technique (see P. H. Lagrange, G. B. Mackaness and T. E. Mille: "J. Exp. Med.", 139, 1529–1539 (1974)) using mice immunized with sheep red blood cells as the antigen.

Thus, 10⁸ sheep red blood cells suspended in 0.05 ml of physiological saline solution were immunized by subcutaneous injection to the one side of dd/Y mice hind footpad (5 mice per group, female, 6-weeks old) to establish delayed-type hypersensitivity. At the same time as this immunization, 1 mg/mouse, 250 mcg/mouse, 62.5 mcg/mouse or 15.6 mcg/mouse of esterastin were intraperitoneally injected to each test mouse. Four days later, 10⁸ sheep rod blood cells were injected subcutaneously into the other side of each test mouse footpad for elicitation of D.T.H. response. 24 Hours after the eliciting injection, the thickness (in mm) of the footpad was measured to evaluate the degree of the swelling in the footpad which received the eliciting injection of sheep rod blood cells. The extent of the swelling in the footpad serves as a measure to estimate the cellular immunity involved. The test results obtained are shown in Table 3 below.

TABLE 3

Effect of esterastin on establishment of D.T.H. to SRBC in mice

| Immunization | Dose of esterastin | Eliciting injection immunization | Increase of footpad thickness (× 0.1 mm) |
|---|---|---|---|
| 10⁸ SRBC | 0 (control) | 10⁸ SRBC | 8.0 |
| " | 1 mg | " | 3.8 |
| " | 250 mcg | " | 3.0 |
| " | 62.5 mcg | " | 6.2 |

Note:
SRBC denotes sheep red blood cells.

From the results of the above table, it is found that administration of 1 mg to 250 mcg of esterastin to mice remarkably suppresses the development of D.T.H. and hence that esterastin shows also the suppressive effect on cellular immunity.

From further tests, it is also found that esterastin at a concentration of 10 mcg/ml exhibits no cell toxicity to the cultured cells. As described hereinbefore, dosage of 250 mg/kg of esterastin does not give any sympton of toxicity at all in the test of estimating acute toxicity in mice.

These and abovementioned results show that esterastin is useful as an immunosuppressive drug which may be utilized with high safety, on the ground that esterastin functions in an entirely different way from the previously known immunosuppressive drugs, for example, 6-mercaptopurine, azathiopurine, cyclophosphamide and corticosteroids of which the cell toxicity is high and is contributing to their effect of suppressing the immunity in animals. For these reasons esterastin may be used as a drug for treating many diseases such as contact allergic dermatitis, systemic lupus erythematosus, autoimmune hemolytic anemia, periarteritis nodosa, myasthenia gravis, arthritis, rheumatism and multiple sclerosis, and it may be used as an agent to suppress the rejection syndrome in the surgical operations of transplantation of internal organs such as the heart and kidneys.

According to this invention, therefore, there is provided an immunosuppressive drug for reducing the immune response in animals including man, which comprises an effective amount of esterastin as the active ingredient, in association with a pharmaceutically acceptable carrier for the active ingredient.

There is further provided by the present invention the method for chemotherapeutically treating immune diseases and disorders which comprises administering to a living animal a pharmaceutical composition to suppress the immune response comprising an effective amount of a suppressing compound of the formula

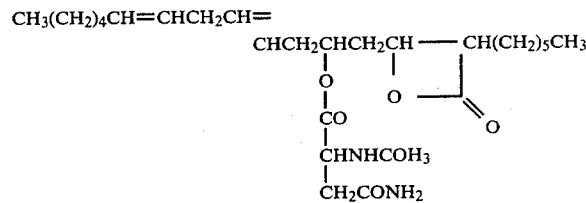

in combination with a pharmaceutically acceptable nontoxic carrier.

The immunosuppressive drug of this invention may be formulated as conventional orally administerable forms such as tablets, capsules, powders, solutions and suspensions, either by admixing an amount of esterastin with a conventional pharmaceutically acceptable solid carrier such as starch, sucrose, talc and calcium carbonate or by dissolving or suspending an amount of esterastin in a pharmaceutically acceptable liquid carrier such as ethanol and water. The proportion of esterastin to the solid or liquid carrier may be chosen appropriately depending on the form of the orally administerable formulation prepared and usually may be in a ratio of from 1:1 to 1:100 by weight.

The immunosuppressive drug of this invention may also be formulated into injectable solutions or suspensions by dissolving or suspending esterastin at a suitable level of from 0.1% to 10% by weight into a physiological saline solution or other conventional pharmaceutically acceptable liquid vehicle such as Ringer's solution, with or without aid of a suitable dispersion agent. The injectable solution or suspension so prepared may be given, eg. by intravenous injection, intramuscular injection or intraperitoneal injection.

It will be appreciated that the actual preferred dosage of esterastin used will vary according to the particular composition formulated for administration, the mode of administration and the particular disease to be treated. Many factors that modify the action of the drug of this invention will be taken into account by the skilled in the art, for example, age, body weight, sex, diet, time of administration, route of administration, rate of excretion, drug combinations, reaction sensitivities and severity of the disease. Generally, about 0.5 mg/kg to about 100 mg/kg of esterastin is given a day to an adult person. Optimal dosages for a given set of conditions of a patient can be ascertained by the skilled in the art using conventional dosage determination tests in view of the above guidelines and in view of the past experiences as obtained when determining suitable dosages of the previously known immunosuppressive drugs such as Imuran (6-mercaptopurine).

It is believed that using the preceding description and without further elaboration, one skilled in the art can utilize the concept of this invention to its full extent. The following preferred specific embodiments are, therefore, to be construed as merely illustrative of this invention.

EXAMPLE 1

A loopful amount of a slant culture of Streptomyces MD4-Cl strain (identified as FERM-P 3723 or ATCC. No. 31336) as the esterastin-producing strain was inoculated to 15 liters of a culture medium comprising 1.5% glycerin, 1.5% cotton seed meal, 0.2% L-asparagine and 0.3% sodium chloride which had been placed in 100 cc. portions in rotary flasks of 500 cc. capacity and which had been sterilized by heating at 120° C. for 20 minutes. The incubation was conducted for consecutive 10 days at 27° C. and at a rotation speed of 180 r.p.m., while samples were taken out of the incubated medium at intervals and each sample was assayed for the potency of esterastin to observe how the production of esterastin proceeded during the incubation period. On the 2nd day of incubation, the production of esterastin reached a maximum, and the level of the esterase-inhibiting substance in the incubation medium kept at a plateau up to the 5th day of incubation. Thereafter, the level of esterastin fell down slowly. The pH value of the incubated medium varied from 6.8 on the 1st day, to 7.2 on the 2nd day, to 7.3 on the 3rd day, to 7.5 on the 4th day and to 6.4 on the 5th day of incubation and subsequently fluctuated in the range of 8.0–9.0 after the 6th day of incubation.

On the 3rd day of incubation, the larger portion of the incubated medium was filtered with aid of a filtration-aid (diatomaceous earth commercially available under a trade name "Hyflo-Supercel") and a clear broth filtrate (12600 ml) was obtained. This broth filtrate was assayed and was found to contain the esterase-inhibiting substance at such a titre that 0.0017 ml of said broth filtrate per ml showed 50% inhibtion ($ID_{50}$) of esterase. This broth filtrate was admixed with 500 ml of butyl acetate for the extraction of the esterase-inhibitory substance therefrom. The remaining aqueous phase was again extracted with 250 ml of butyl acetate. The combined extracts in butyl acetate was concentrated to dryness under reduced pressure to give 200 mg of a brown colored powder. The $ID_{50}$ of this powder was 0.03 mcg/ml as determined by the assay method as stated hereinbefore. The efficiency of extraction of the active substance from the broth filtrate by means of butyl acetate was about 80%.

EXAMPLE 2

Streptomyces MD4-Cl strain was incubated for 3 days using the culture medium and cultivation conditions same as those of Example 1. The resulting fermentation broth was filtered to remove the mycelia cake. The mycelia cake (280 g) was extracted twice with methanol, that is, with 1500 ml of methanol and then with 500 ml of methanol. The combined methanolic extracts were concentrated to dryness under reduced pressure. The solid residue obtained was dissolved in 500 ml of water and the aqueous solution was extracted with 500 ml and 200 ml of butyl acetate successively in that order, so that about 90% or more of the esterastin originally present in the solid residue was transferred into solution in the butyl acetate phase. The butyl acetate extracts were combined together and concentrated to dryness under reduced pressure to give 3 g of a brown powder. This powder had a potency that its $ID_{50}$ to esterase was 0.07 mcg/ml.

EXAMPLE 3

Streptomyces MD4-Cl strain was cultivated for 3 days using the same culture medium and incubation conditions as those of Example 1, and the fermentation broth filtrate (10 l) so obtained was passed through a column of 1 l of Amberlite XAD-4 (an adsorbent resin, a product of Rohm & Haas Co., U.S.A.) to adsorb esterastin on the resin. The effluent running out of the resin column had no activity to inhibit esterase. The adsorbed esterastin was recovered from the resin by eluting with 2 l of methanol. The methanolic eluate was collected in 20 g-fractions, and the active fractions were combined together and concentrated to dryness under reduced pressure to afford 160 mg of a crude powder of esterastin ($ID_{50}=0.03$ mcg/ml). Yield: more than 90%.

EXAMPLE 4

A seed culture which was obtained by incubating Streptomyces MD4-Cl strain for 3 days in the same culture medium and under the same incubation conditions as those of Example 1 was inoculated in 400 ml-portions into two jar-fermenters of 30l-capacity each containing 15 l of a culture medium comprising 1.5% glycerin, 1.5% cotton seed meal, 0.2% L-asparagine and 0.3% sodium chloride which had been sterilized. The jar cultivation was then conducted for 3 days at 27° C. at a rate of aeration of 15 l/minutes and at an agitator speed of 250 r.p.m. In this way, there was obtained a culture broth of a potency such that its $ID_{50}$ to esterase was 0.0017 ml/ml. The two jar fermenters together gave 30 l of the culture broth. Filtration of this culture broth afforded 780 g of mycelium cake which was then extracted twice each with 4 l portion of methanol. The combined methanolic extracts (8 l in total) were concentrated to dryness under reduced pressure to give 17.5 g of a crude powder of esterastin. This crude powder was subjected to two operations of the liquid distribution method using 1 l of water and 1 l of butyl acetate for each run. The resulting butyl acetate extracts were combined together (2 l in total) and concentrated to dryness under reduced pressure to yield 6.5 g of a crude powder of esterastin ($ID_{50}=0.1$ mcg/ml).

EXAMPLE 5

The crude powder (6.5 g, $ID_{50}=0.1$ mcg/ml) obtained in Example 4 was extracted with 200 ml and then with 100 ml of chloroform. The extracts in chloroform were combined together and concentrated to a volume of 100 ml under reduced pressure. The concentrated solution was admixed with 10 g of silica gel (commercially available under a trade name "Wako-gel C-100", a product of Wako Chemicals Co., Japan), and the admixture was concentrated to dryness under reduced pressure, so that esterastin was adsorbed by the silica gel. The silica gel containing esterastin adsorbed therein was placed at the top of a chromatographing column of 300 ml of silica gel which had been washed with chloroform. After the whole column was washed with 3 l of chloroform, the elution was made using a mixed solvent consisting of chloroform-methanol (80:1 by volume). The eluate was collected in 20 g-fractions, and the packs of the esterase-inhibiting activity appeared in the vicinity of the fractions Nos. 60 to 160. These active fractions were concentrated to dryness under reduced pressure to give 150 mg of a lightly red colored powder. This powder showed a potency such that its $ID_{50}$ to esterase was 0.0024 mcg/ml.

EXAMPLE 6

The lightly red colored powder of esterastin (150 mg) obtained in Example 5 was dissolved in 2 ml of methanol and then chromatographed in a column of 400 ml of Sephadex LH-20 which had been swollen with methanol. The elution was made using methanol as the eluent, and the eluate was collected in 5 g-fractions. The peaks of the esterase-inhibiting activity appeared in the vicinity of the fractions Nos. 54 to 66. These active fractions were concentrated to dryness under reduced pressure to give 30 mg of a yellow colored powder. This powder showed a potency such that its $ID_{50}$ to esterase was 0.0007 mcg/ml.

EXAMPLE 7

The yellow powder (30 mg) obtained in Example 6 was dissolved in 1 ml of ethyl acetate, and the resulting solution admixed with 500 mg of silica gel (Wako-gel C-200). The admixture was concentrated to dryness under reduced pressure, so that esterastin was adsorbed by the silica gel mass. This silica gel mass was placed at the top of a chromatographying column (1.2 cm in diameter and 20 cm in height) of dry silica gel, and the elution was made with ethyl acetate as the eluent. The eluate was collected in 10 g-fractions, and esterastin appeared solely in the vicinity of the fractions Nos. 10 to 17. These active fractions Nos. 10–17 were concentrated to dryness under reduced pressure to give 7 mg of a colorless powder of esterastin, m.p. 90°–95° C. This powder showed a potency such that its $ID_{50}$ to esterase was 0.0002 mcg/ml.

EXAMPLE 8

A culture medium (300 l) comprising 1.5% glycerin, 1.5% cotton seed meal, 0.3% sodium chloride, 0.2% L-asparagine and 0.005% antifoaming agent (polyoxyalkylene commercially available under a tradename "Adecanol", a product of Asahi Denka Co., Japan) was charged in a stainless steel tank of 570 l capacity and then sterilized by heating at 120° C. for 20 minutes. To this sterilized culture medium was inoculated 30 l of a seed culture which was obtained by incubating Streptomyces MD4-Cl strain (FERM-P 3723) for 2 days at 27° C. under aeration and agitation. The inoculated culture medium was incubated at 27° C. for 48 hours at a rate of aeration of 300 l/minutes and at an agitator speed of 200 r.p.m. The fermentation broth so obtained was filtered to give 34.2 kg of the filter cake containing the mycelia. This filter cake was extracted twice each with 100 l of ethanol, and the combined ethanolic extracts were concentrated to a volume of 6 l under reduced pressure. The concentrated solution was extracted twice each with 6 l of butyl acetate. The extracts in butyl acetate were combined together and concentrated under reduced pressure to give 128.2 g of a crude powder of esterastin which had a potency corresponding to an $ID_{50}$ value of 0.08 mcg/ml.

EXAMPLE 9

The crude powder of esterastin obtained in Example 8 was purified in the following procedure. This crude powder (128.2 g) was dissolved in 500 ml of chloroform and the resultant solution was passed through a column of 1.5 kg of silica gel (Wako-gel C-100) for adsorption of esterastin. The silica gel column was washed with 10 l of chloroform and then with 10 l of chloroform-methanol (100:1 by volume), followed by elution with chloroform-methanol (80:1 by volume). The active fractions (2500 ml) of the eluate were combined together and concentrated to dryness under reduced pressure to afford 4.83 g of a brown colored crude powder which had a potency corresponding to an $ID_{50}$ value of 0.002 mcg/ml. This crude powder was taken up into 20 ml of methanol and the solution obtained was passed through a column of 2 l of Sephadex LH-20 which had been swollen with methanol. This column was then eluted with 4 l of methanol. The active fractions of the eluate were combined together and concentrated to dryness under reduced pressure to yield 656 mg of a lightly yellow colored powder ($ID_{50}=0.0004$ mcg/ml). This powder was taken up into 5 ml of ethyl acetate and the solution obtained was passed through a column of 250 g of silica gel (Wako-gel C-300) for adsorption of esterastin. This silica gel volumn was then developed with ethyl acetate, and the active fractions of the eluate were combined together (1000 ml) and concentrated to dryness under reduced pressure, affording 351 mg of a colorless powder of esterastin which had a potency corresponding to an $ID_{50}$ value (to esterase) of 0.0002 mcg/ml.

We claim:

1. The process for the production of the compound having the formula

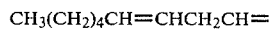
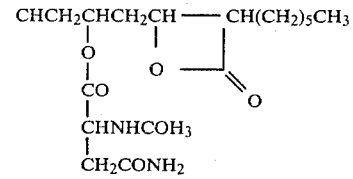

denominated esterastin, which comprises cultivating an esterastin-producing strain of Streptomyces lavendulae having the identifying characteristics of A.T.C.C. 31336 under submerged aerobic conditions in a nutrient medium containing assimilable carbon and nitrogen sources for a period of time sufficient to produce a substantial amount of esterastin in the culture medium and recovering esterastin from said medium.

2. A process according to claim 1 in which the esterastin-producing strain is Streptomyces ATCC 31336.

3. A process according to claim 1 in which the microorganism is cultivated at a temperature of 27° C. to 37° C. under aerobic conditions.

4. A process according to claim 1 in which the microorganism is cultivated at a temperature of 25° C. to 35° C. for a period of 2 to 4 days under aerobic conditions.